United States Patent
Jedema et al.

(10) Patent No.: US 9,184,469 B2
(45) Date of Patent: Nov. 10, 2015

(54) BATTERY

(75) Inventors: Friso Jacobus Jedema, Eindhoven (NL); Willem Frederik Adrianus Besling, Eindhoven (NL); Freddy Roozeboom, Waalre (NL); René Wilhelmus Johannes Maria van den Boomen, Asten (NL); Freek Egbert van Straten, Mook (NL)

(73) Assignee: NXP B.V., Eindhoven (NL)

( * ) Notice: Subject to any disclaimer, the term of this patent is extended or adjusted under 35 U.S.C. 154(b) by 746 days.

(21) Appl. No.: 13/287,916

(22) Filed: Nov. 2, 2011

(65) Prior Publication Data
US 2012/0116189 A1 May 10, 2012

(30) Foreign Application Priority Data
Nov. 3, 2010 (EP) .................................... 10189866

(51) Int. Cl.
*H01M 2/10* (2006.01)
*H01M 2/20* (2006.01)
*H01M 2/22* (2006.01)
*H01M 2/24* (2006.01)
*H01M 10/0583* (2010.01)
*H01M 10/04* (2006.01)
*H01M 10/052* (2010.01)
*A61B 5/00* (2006.01)
*A61B 5/01* (2006.01)
*A61B 5/145* (2006.01)

(52) U.S. Cl.
CPC .......... *H01M 10/0583* (2013.01); *H01M 2/204* (2013.01); *H01M 10/0436* (2013.01); *H01M 10/052* (2013.01); *A61B 5/0031* (2013.01); *A61B 5/01* (2013.01); *A61B 5/14539* (2013.01); *A61B 5/14542* (2013.01); *A61B 5/14546* (2013.01); *A61B 2560/0214* (2013.01); *Y02E 60/122* (2013.01); *Y10T 29/49107* (2015.01)

(58) Field of Classification Search
USPC ................................ 429/149–160, 163–187; 29/623.1–623.5; 600/309
See application file for complete search history.

(56) References Cited

U.S. PATENT DOCUMENTS

| 2,745,894 | A | 5/1956 | Nowotny |
| 2,798,895 | A | 7/1957 | Nowotny |
| 2,870,235 | A | 1/1959 | Soltis |
| 6,045,943 | A | 4/2000 | Nowaczyk |
| 6,641,952 | B2 * | 11/2003 | Maple ........................... 429/157 |
| 7,198,866 | B2 * | 4/2007 | Miyamoto et al. ............ 429/149 |

(Continued)

FOREIGN PATENT DOCUMENTS

EP  2 123 325 A2  11/2009
WO  01/59870 A1  8/2001

(Continued)

OTHER PUBLICATIONS

Extended European Search Report for Patent Appln. No. 10189866.6 (Feb. 25, 2011).

*Primary Examiner* — Basia Ridley
*Assistant Examiner* — Caitlin Wilmot

(57) ABSTRACT

A battery comprises a carrier foil, with solid state battery elements spaced along the foil and mounted on opposite sides of the foil in pairs, with the battery elements of a pair mounted at the same position along the foil. The carrier foil is folded to define a meander pattern with battery element pairs that are adjacent each other along the foil arranged back to back.

18 Claims, 4 Drawing Sheets

(56) References Cited

U.S. PATENT DOCUMENTS

| | | | |
|---|---|---|---|
| 8,338,036 B2 * | 12/2012 | Doi | ............... 429/304 |
| 2005/0191545 A1 | 9/2005 | Bowles et al. | |
| 2006/0166086 A1 | 7/2006 | Kato | |
| 2006/0271112 A1 | 11/2006 | Martinson et al. | |
| 2007/0020516 A1 | 1/2007 | Yoon | |
| 2007/0026309 A1 | 2/2007 | Notten et al. | |
| 2007/0252556 A1 | 11/2007 | West et al. | |
| 2008/0241703 A1 | 10/2008 | Yamamoto et al. | |
| 2009/0023057 A1 | 1/2009 | Kim | |
| 2011/0117417 A1 * | 5/2011 | Pitts | ............... 429/149 |
| 2013/0273413 A1 | 10/2013 | Fahlgren et al. | |

FOREIGN PATENT DOCUMENTS

| | | |
|---|---|---|
| WO | 02/03493 A1 | 1/2002 |
| WO | 2004/114397 A1 | 12/2004 |
| WO | 2007/070717 A2 | 6/2007 |
| WO | 2008/015593 A2 | 2/2008 |

* cited by examiner

BATTERY

This application claims the priority under 35 U.S.C. §119 of European patent application no. 10189866.6, filed on Nov. 3, 2010, the contents of which are incorporated by reference herein.

FIELD OF THE INVENTION

This invention relates to batteries, and particularly low volume high energy density batteries.

BACKGROUND OF THE INVENTION

Rechargeable Li-ion batteries have found widespread application as a result of their low self-discharge rate, large cycle numbers and their ability to provide an indication of the remaining energy capacity.

Different applications have different requirements for the volumetric energy density, but there is always a desire to increase this, to enable smaller devices to function.

For example, for the power supply requirements of medical implanted devices, it is anticipated that the achieved volumetric energy density (Wh/L) is more important than the cost price of energy ($/Wh).

For such implantable batteries, a volume between 10 to 100 mm3 is desired.

For small batteries such as this, the volumetric energy density decreases rapidly, because the packaging takes up a larger fraction of the battery volume. An illustration of this is shown in FIG. 1, where the volumetric energy of miniaturized batteries is shown as a function of their battery volume.

One current battery considered to be at the cutting edge of technology is the Eagle Pitcher Contego 500 µAh. This is one of the smallest batteries currently known, developed for the medical implantation market. It has an energy capacity of 1.8 mWh and a volume of 30 mm3. The volumetric energy density is thus 60 Wh/L.

For medical applications, it is advantageous if the implanted device can be fully autonomous for an extended period of time (i.e. one week or longer). This will limit the risks of suffering malfunctions in the implanted devices due to a discontinuous power supply, and may also avoid the extra technical complexity of recharging efforts. If recharging efforts could be minimized, the patient could more easily leave the hospital, while the implanted device continues to do its work (e.g. for sensing & monitoring body functions).

The largest power drain for an implanted device will be caused by the need to communicate the information, as obtained by the implanted device, to the outside world and to let the outside world know that the implanted device is still operational.

For this purpose an ultra low power (ULP) radio is needed. A ULP radio typically needs a continuous power of around 70 µWatt. This means that the medical implanted device, powered by an Eagle Pitcher Contego 500 µAh battery, can only power the ULP radio for 1 day without recharging efforts. This is still typically too short for a patient to leave the hospital in a convenient manner.

SUMMARY OF THE INVENTION

According to the invention, there is provided a battery, comprising:

a carrier foil, with solid state battery elements spaced along the foil and mounted on opposite sides of the foil in pairs, with the battery elements of a pair mounted at the same position along the foil, wherein the carrier foil is folded to define a stack of battery elements in a meander pattern with battery element pairs that are adjacent each other along the foil arranged back to back in the stack.

This design results in a stack with the foil interposed between successive pairs of battery elements. This means the foil volume can be kept to a minimum thereby to keep the energy density as high as possible.

The foil can comprise support sections to which the pairs of battery elements are mounted, and connection wires between the support sections. This makes the battery foil easier to fold and reduces weight.

The battery elements can be mounted on the support sections parallel to the elongate axis of the foil, or they may be mounted on the support sections at an angle between 0 and 45 degrees to an elongate length axis of the foil. This further facilitates the folding operation.

The foil can comprise a polyimide flexible PCB. This gives the required flexibility for the folding. The foil can be less than 50 µm thick, and may be less than 30 µm thick, again to take up minimum volume.

The battery elements preferably comprise Li-ion battery elements.

The battery elements can be electrically connected in series, parallel or a combination thereof.

The battery can be used in a medical implant or electronic pill, comprising a sensor or actuator powered by the battery.

The sensor or actuator can comprise a chemical sensor, a biological sensor, a physical sensor or an electrochemical sensor.

The invention also provides a method of forming a battery, comprising:

spacing solid state battery elements along carrier foil, with solid state battery elements mounted on opposite sides of the foil in pairs, with the battery elements of a pair mounted at the same position along the foil; and folding the carrier foil to define a stack of battery elements in a meander pattern with battery element pairs that are adjacent each other along the foil arranged back to back in the stack.

BRIEF DESCRIPTION OF THE DRAWINGS

Examples of the invention will now be described in detail with reference to the accompanying drawings, in which.

DETAILED DESCRIPTION OF EMBODIMENTS

The invention relates to a packaging approach for battery elements. While the approach can be used with any solid state battery elements, the invention is of particular interest for 3D Li-ion solid state battery elements, for example as disclosed in US20070026309.

Figure 1:
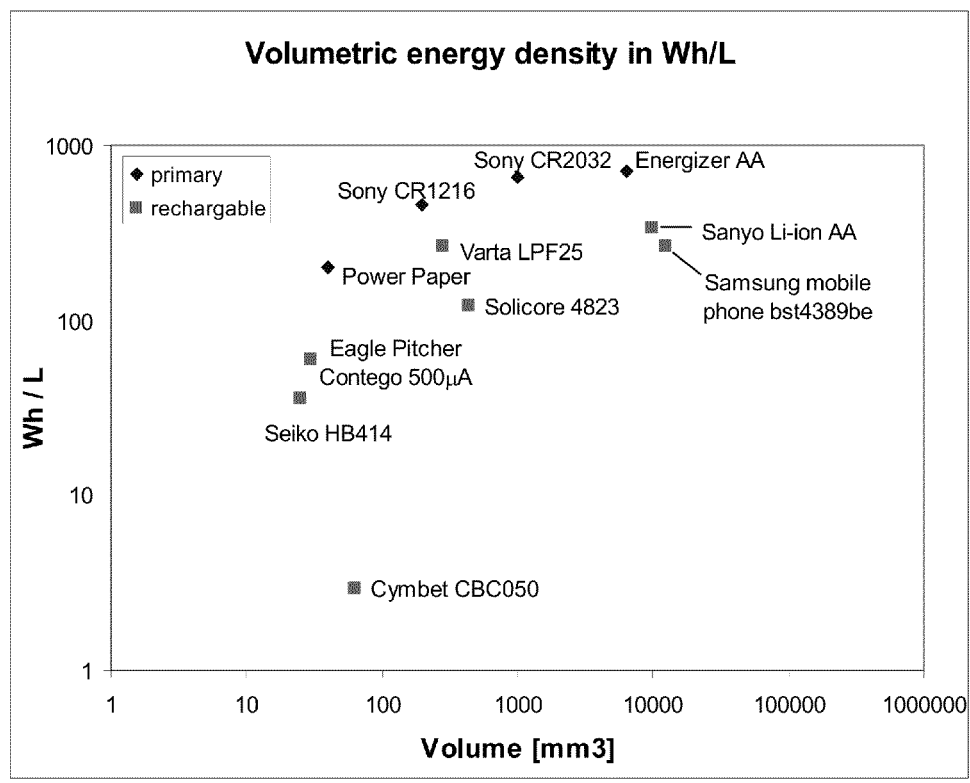
FIG. 1 shows the relationship between the energy density of a range of existing batteries and the volume.
Figure 2:
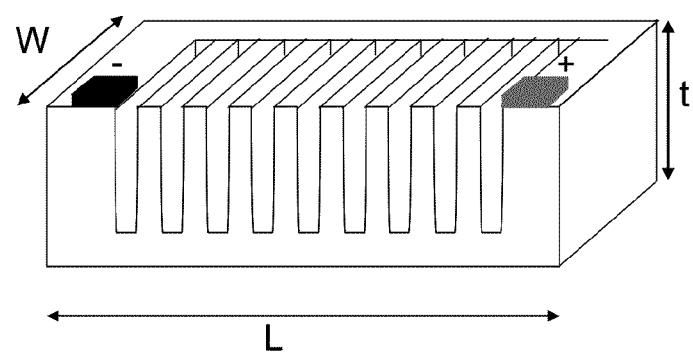
FIG. 2 shows the basic design of a known Li-ion battery element.

FIG. 2 is a schematic drawing of a 3D Li-ion solid state battery, of the type disclosed in US20070026309. The battery element comprises etched trenches in a Si substrate which form a harmonic or meandering wave, which enhances the total energy capacity per Si footprint.

The maximum total energy capacity for such a 3D Li-ion battery element is anticipated to be 13 mWh for 1 cm² of Si area (W×L) and a thickness t of 100 μm.

The invention uses solid state battery elements spaced along a foil and mounted on opposite sides of the foil in pairs. The carrier foil is folded to define a meander pattern with battery element pairs that are adjacent to each other along the foil arranged back to back.

Figure 3:
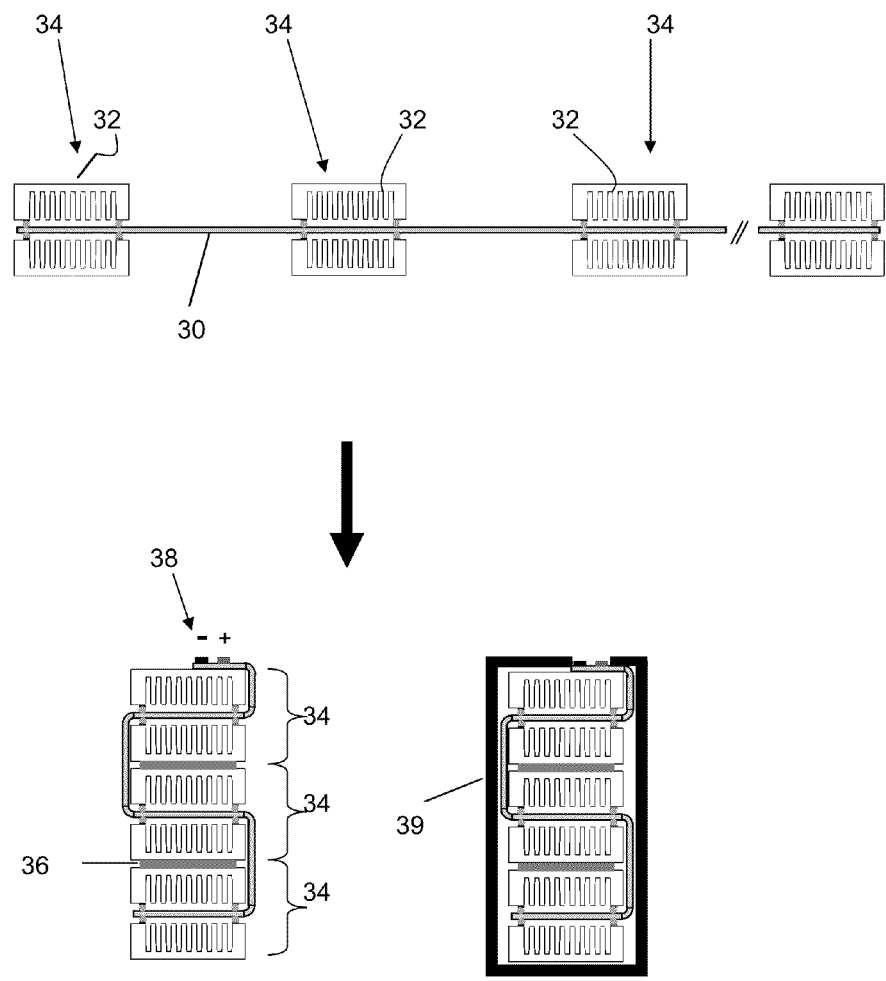
FIG. 3 shows a battery of the invention.

FIG. 3 shows a design in accordance with the invention.

A foil 30 has conductive tracks on both sides. It can comprise a polyimide PCB foil for example 20 μm thick, with printed copper wiring. Foils with copper routing layouts are already present in the back-end industry.

Battery elements 32 are mounted along the foil. The battery elements are in pairs 34. The battery elements 32 of a pair 34 are mounted opposite each other, and therefore at the same position along the foil. The pairs are spaced, so that the foil area between the pairs can be bent and folded to form a package.

The way the foil is folded is shown in the lower part of FIG. 3.

A meander pattern is defined with battery element pairs 34 that are adjacent each other along the foil arranged back to back in a stack. By back-to back is meant the pairs are oppositely oriented. For example, from the top to the bottom of the stack, the battery elements are in a sequence TBBTTB, where T is a battery element that was on top of the foil before folding, and B is a battery element that was on the bottom of the foil before folding. The first pair is in the order TB, the second pair in the order BT and the third in the order TB.

The back to back pairs are glued together by glue 36. The terminals 38 to the battery are on one side of the foil so that they are exposed to the exterior in the folded battery.

FIG. 3 shows that the folded battery can be encased in an encapsulation 39.

The folded arrangement shown can be considered to be a double harmonica or meandering structure. This arrangement achieves the highest volumetric energy density possible for volumes between 10 to 100 mm³, reaching about 1300 Wh/L. With a thickness of each battery element of t=100 μm, the volumetric energy density per element is 13 mWh/1 cm²/100 μm=1300 Wh/L. The solution offers a large flexibility on the particular dimensions of the battery, as would be desired by a customer.

For example, a battery volume of 30 mm³ would yield a total energy capacity of about 39 mWh with this solution, as compared to the 1.8 mWh of the Eagle Pitcher Contego 500 μAh battery. This can be realized for example by stacking 24 battery elements with a physical size of W=2.4 mm, L=5.2 mm and t=0.1 mm (each element having a 1.6 mWh energy capacity) in a volume of 2.4 mm×2.4 mm×5.2 mm (=30 mm³).

With the battery of the above example (39 mWh), a medical implanted device can operate for 22 days without recharging effort, while having a continuously operating ULP radio (72 μW) on board.

This enables the patient to leave the hospital for quite some time, without having to worry about power discontinuation. This can create significant value because travelling time and the time spent in the hospital is much reduced.

In one implementation, the battery elements are electrically connected in parallel. This increases the total energy capacity, while having a similar voltage available (such as 3.9 V) for the stacked battery, as the voltage of a single element.

However, the battery elements could also be electrically connected in series, thereby increasing not only the capacity, but also the output voltage of the stacked battery. This could be an additional advantage for other applications, as for example display drivers that require 15 V.

A combination of parallel and serial connections would enable a very flexible tailoring of output voltage in exchange for the total amount of current capacity available.

Figure 4:
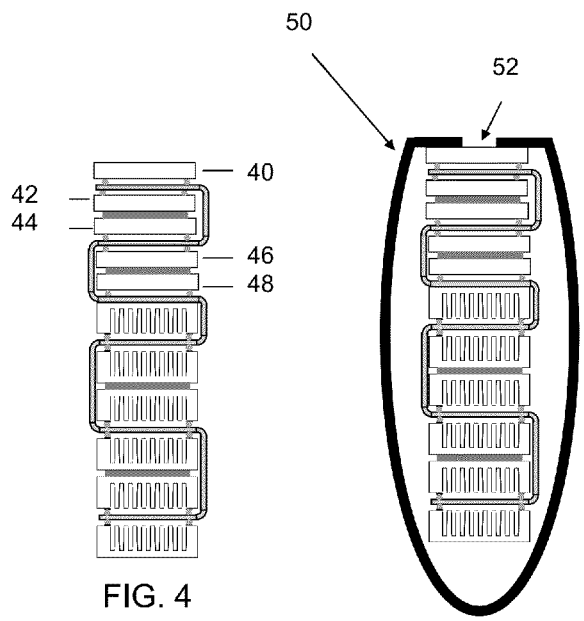
FIG. 4 shows the use of the battery of FIG. 3 in a medical device for use inside the body.

The arrangement of the invention can be adapted to allow all kinds of other elements, preferably manufactured on Si substrates, to be incorporated, as is shown in FIG. 4.

FIG. 4 shows an electronic pill monitoring device.

Additional components include a sensor 40, memory 42 (such as SRAM or non-volatile Flash or PCRAM), energy conversion system 44 (for example for deriving energy from blood glucose by oxidation), signal processor 46 and wireless communications circuit 48 (such as an ULP radio). The communications circuit can be permanently in the 'on' state or can be activated by an external signal, e.g. generated by Near Field Communication (NFC) or Infrared.

The additional components are mounted on the foil before folding, and they can have the same 2D shape (but not necessarily the same depth) as the battery elements so that the resulting folded structure is still a stack with uniform sides (i.e. a cuboid). The combination of battery and other components is mounted in a biocompatible coating 50 such as parylene. An opening 52 is shown for exposing a sensor area.

The monitoring device can use a chemical sensor (e.g. for $O_2$ monitoring), a biological sensor (e.g. for biomarker monitoring of molecular targets such as DNA, RNA, metabolytes, viruses, proteins, enzymes, hormones, peptides, nucleic acids and cellular targets such as pathogen cells, bacterial cells and fungal cells), a physical sensor (e.g. for temperature monitoring), or an electrochemical sensor (e.g. pH sensor). It may instead (or additionally) have an actuator for example for payload release in an e-pill.

Figure 5:
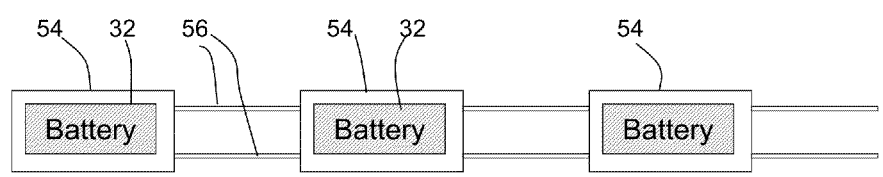
FIG. 5 shows a first alternative to the foil arrangement of the design of FIG. 3.

FIG. 5 shows a variation to the foil design, in which the foil comprises support sections 54 to which the pairs of battery elements 32 are mounted (on both sides), and connection wires 56 between the support sections. There are two connection wires shown, to connect the positive and negative terminals of each battery element (in series or in parallel as desired).

The wires function as bending legs and enable an more flexible folding in addition to reducing the amount of material. The wires may be copper tracks on a narrow part of the foil, or they may be actual wires that connect separate foil areas together.

Figure 6:
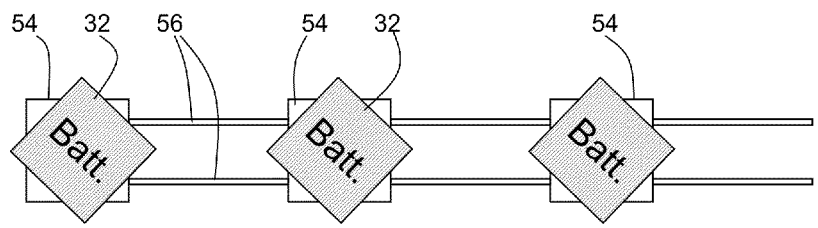
FIG. 6 shows a second alternative to the foil arrangement of the design of FIG. 3.

FIG. 6 shows another variation to the foil design, again with support sections 54 to which the pairs of battery elements 32 are mounted (on both sides), and connection wires 56 between the support sections. The battery elements are mounted at 45 degrees in this particular example to the elongate foil axis. The rotation of the battery elements relative to the elongate foil axis creates a secure cavity for the bending legs of the foil, containing the electrical wiring between the elements. This could protect the wiring better from mechanical disturbances during manufacturing. Clearly a trade off exists between the amount of space in the secure cavity (packaging volume loss) and reliability of the wiring as required for the specific applications.

FIG. 5 shows a folding with minimum packaging volume loss, whereas FIG. 6 shows the folding with the maximum packaging volume loss (corresponding to a 45 degrees rotation) and higher wiring reliability.

By stacking 3D Li-ion solid state batteries using the approach of the invention, a volumetric energy density of about 1300 Wh/L in volumes of 10 to 100 mm3 can be achieved. This is more than a factor of 22 better than the current state of the art for a battery volume of 30 mm3. The much higher volumetric energy density results in a significant competitive advantage for batteries used for in-vivo medical applications. The disclosed device and fabrication method further allows an easy modular incorporation of functional modules for medical implants, powered by the stacked batteries.

The invention is of particular interest for batteries with a volume below 100 mm3 and more preferably below 50 mm3, for example around 30 mm3. As the volume is reduced, the packaging efficiency becomes more critical.

Each battery element typically has an area less than 50 mm2 and a thickness less than 0.5 mm, and the stack will typically include at least 4 battery elements, up to around 50 battery elements.

There are numerous applications for the battery outside the medical field:
remote sensors generally;
powered smart cards, for example for display functions
powered security applications in passports and other identity cards.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A battery arrangement, comprising:
a carrier foil having a top major surface and a bottom major surface opposite the top major surface, wherein the top major surface faces up when the bottom major surface faces down, with solid state batteries spaced along the carrier foil and mounted on the opposite major surfaces of the carrier foil in pairs, with the solid state batteries of each pair mounted at the same position along the length of the carrier foil but on the opposite major surfaces of the carrier foil,
wherein the carrier foil is folded to define a stack of solid state batteries in a meander pattern with battery pairs that are adjacent each other along the carrier foil arranged back to back in the stack;
wherein the solid state batteries are electrically connected in series or parallel or a combination thereof by conductive tracks on the carrier foil or by connection wires.

2. A battery arrangement as claimed in claim 1, wherein the carrier foil comprises support sections to which the pairs of solid state batteries are mounted, and the connection wires are located between the support sections.

3. A battery arrangement as claimed in claim 2, wherein the solid state batteries are mounted on the support sections at an angle of 45 degrees to an elongate length axis of the carrier foil.

4. A battery arrangement as claimed in claim 1, wherein the carrier foil comprises a polyimide flexible PCB.

5. A battery as claimed in claim 1, wherein the solid state batteries are Li-ion batteries.

6. A battery arrangement as claimed in claim 1, wherein the solid state batteries are electrically connected in series.

7. A battery arrangement as claimed in claim 1, wherein the solid state batteries are electrically connected in parallel.

8. A medical implant or electronic pill, comprising:
a battery arrangement as claimed in claim 1; and
a sensor or actuator powered by the battery arrangement.

9. A medical implant or electronic pill as claimed in claim 8, wherein the sensor or actuator comprises:
a chemical sensor, a biological sensor, a physical sensor or an electrochemical sensor.

10. A method of forming a battery arrangement, comprising:
spacing solid state batteries along a carrier foil that has a top major surface and a bottom major surface opposite the top major surface, wherein the top major surface faces up when the bottom major surface faces down, with the solid state batteries mounted on the opposite major surfaces of the carrier foil in pairs, with the solid state batteries of each pair mounted at the same position along the length of the carrier foil but on the opposite major surfaces of the carrier foil; and
electrically connecting the solid state batteries in series or parallel or a combination thereof using conductive tracks on the carrier foil or by connection wires;
after the solid state batteries have been electrically connected in series or parallel or a combination thereof, folding the carrier foil to define a stack of solid state batteries in a meander pattern with battery pairs that are adjacent each other along the carrier foil arranged back to back in the stack.

11. A method as claimed in claim 10, wherein the carrier foil comprises a polyimide flexible PCB.

12. A method as claimed in claim 10, wherein the solid state batteries are Li-ion batteries.

13. A method as claimed in claim 10 comprising electrically connecting the solid state batteries in series using a conductive pattern on the carrier foil.

14. A method as claimed in claim 10 comprising electrically connecting the solid state batteries in parallel using a conductive pattern on the carrier foil.

15. A battery arrangement as claimed in claim 2, wherein the solid state batteries are mounted on the support sections at an angle of approximately 45 degrees to an elongate length axis of the carrier foil.

16. A battery arrangement as claimed in claim 1, wherein the conductive tracks on the carrier foil comprise conductive tracks on both sides of the carrier foil at the same position along the length of the carrier foil but on opposite sides of the carrier foil, wherein the conductive tracks on one side of the carrier foil electrically connect the solid state batteries on the one side of the carrier foil and the conductive tracks on the opposite side of the carrier foil electrically connect the solid state batteries on the opposite side of the carrier foil.

17. A battery arrangement as claimed in claim 1, wherein the stacked solid-state batteries that are adjacent to each other along the length of the carrier foil and that are mounted on the same major surface of the carrier foil are glued together by glue.

18. A method as claimed in claim 10, further comprising gluing together the stacked solid-state batteries that are adjacent to each other along the length of the carrier foil and that are mounted on the same major surface of the carrier foil.

* * * * *